United States Patent [19]
Ohsawa et al.

[11] Patent Number: 5,679,496
[45] Date of Patent: Oct. 21, 1997

[54] CHEMICALLY AMPLIFIED POSITIVE RESIST COMPOSITION

[75] Inventors: Youichi Ohsawa; Satoshi Watanabe; Katsuyuki Oikawa, all of Nakakubiki-gun; Akinobu Tanaka, Fujisawa; Yoshio Kawai; Jiro Nakamura, both of Isehara, all of Japan

[73] Assignees: Shin-Etsu Chemical Co., Ltd.; Nippon Telegraph and Telephone Corp., both of Tokyo, Japan

[21] Appl. No.: 566,703

[22] Filed: Dec. 4, 1995

[30] Foreign Application Priority Data

Dec. 5, 1994 [JP] Japan .................. 6-329914

[51] Int. Cl.$^6$ .................. G03F 7/004; G03F 7/26
[52] U.S. Cl. .................. 430/270.1; 430/326; 430/905; 430/910; 522/31; 522/59
[58] Field of Search .................. 430/270.1, 326, 430/905, 910; 522/31, 59

[56] References Cited

U.S. PATENT DOCUMENTS

| | | | |
|---|---|---|---|
| 4,491,628 | 1/1985 | Ito et al. | 430/270.1 |
| 4,883,740 | 11/1989 | Schwalm et al. | 430/270.1 |
| 5,069,998 | 12/1991 | Schwalm et al. | 430/270.1 |
| 5,318,876 | 6/1994 | Schwalm et al. | 430/270.1 |
| 5,403,695 | 4/1995 | Hayase et al. | 430/270.1 |

*Primary Examiner*—John S. Chu
*Attorney, Agent, or Firm*—Millen, White, Zelano, & Branigan, P.C.

[57] ABSTRACT

A chemically amplified positive resist composition contains a novel trifluoromethanesulfonic or p-toluenesulfonic acid sulfonium salt having at least one tert-butoxycarbonylmethoxy group as an acid labile group. The composition is highly sensitive to high energy radiation, especially KrF excimer laser and has high sensitivity, resolution and plasma etching resistance while the resulting resist pattern is heat resistant.

16 Claims, No Drawings

CHEMICALLY AMPLIFIED POSITIVE RESIST COMPOSITION

BACKGROUND OF THE INVENTION

1. Field of the Invention

This invention relates to a chemically amplified positive resist composition containing a novel sulfonium salt. The chemically amplified positive resist composition is highly sensitive to high energy radiation such as deep-ultraviolet line, electron beam and X-rays, can be developed with alkaline aqueous solution to form a pattern, and is thus suitable for use in a fine patterning technique.

2. Prior Art

As the LSI technology tends toward higher integration and higher speed, further refinement of pattern rules is required. The current patterning technology mostly relies on light exposure which is now approaching to the essential limit of resolution which is dictated by the wavelength of a light source. It is generally recognized that in light exposure using g-line (wavelength 436 nm) or i-line (wave-length 365 nm) as a light source, a pattern rule of about 0.5 μm is the limit. For LSIs fabricated by such light exposure technique, a degree of integration equivalent to 16 mega-bit DRAM is the limit. At present, LSIs fabricated in the laboratory have reached this stage. It is urgently required to develop a finer patterning technique.

Under such circumstances, deep-ultraviolet lithography is regarded promising as the next generation of fine patterning technology. The deep-UV lithography is capable of working on the order of 0.3 to 0.4 μm. If a less light absorbing resist is used, it is possible to form a pattern having a side wall nearly perpendicular to the substrate. Great attention is now paid to the technique of utilizing a high illuminance KrF excimer laser as a deep-UV light source. In order to employ this technique on a mass production scale, a resist material having low light absorption and high sensitivity is desired.

From this point of view, a number of chemically amplified positive working resist materials were recently developed using acid catalysts as disclosed in JP-B 27660/1990, JP-A 27829/1988, U.S. Pat. Nos. 4,491,628 and 5,310,619. These materials have high sensitivity, resolution and dry etching resistance and are promising as resist materials especially suited for deep-UV lithography.

It is known that the function of chemically amplified positive resist materials is largely affected by photo acid generators used therein. Typical photo acid generators are onium salts as shown below.

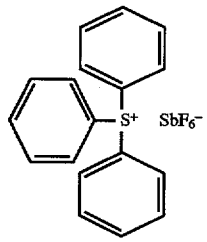

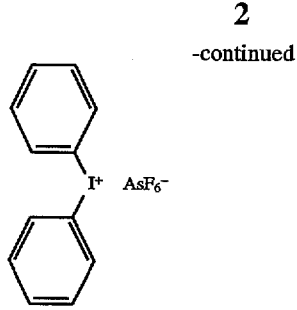

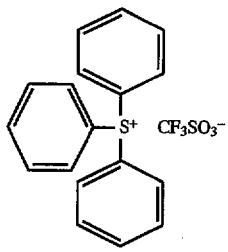

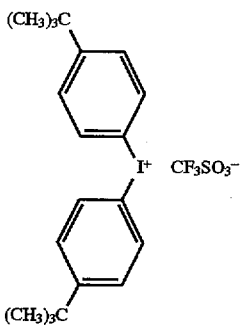

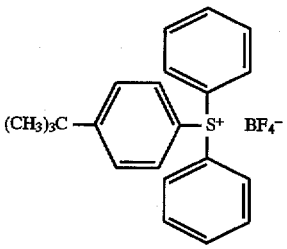

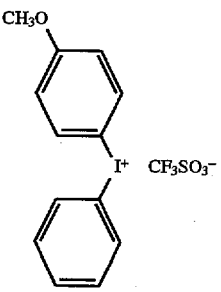

The onium salts themselves are lipophilic. When blended as a resist component, they act to reduce the solubility of the resist material in alkaline aqueous solution and to prevent the resist film from thinning upon development.

However, in exposed areas of positive resist material, photo acid generators absorb high energy radiation to decompose into products which are also lipophilic. This reduces the rate of dissolution of the exposed areas in alkaline aqueous solution, failing to provide a high ratio of the alkali dissolution rate of exposed areas to that of unexposed areas (which ratio is known as dissolution rate contrast). Consequently, chemically amplified positive resists using onium salts as mentioned above are low in resolution upon alkaline development, that is, poor in removal of exposed areas, often resulting in a trapezoidal forward tapered pattern rather than a rectangular pattern.

This problem can be solved by incorporating a tert-butoxycarbonyl group or acid labile group into p-hydroxyphenyl sulfonium salts as disclosed in U.S. Pat. No. 5,191,124 corresponding to JP-A 26550/1989, U.S. Pat. No. 4,883,740 corresponding to JP-A 35433/1989, and U.S. Pat. No. 5,084,371 corresponding to JP-A 12153/1990. Upon exposure to high energy radiation, the salts decompose to generate acids, which help form phenol derivatives having an alkali dissolving ability, providing an enhanced dissolution rate contrast. These sulfonium salts capable of creating phenol derivatives, however, fail to satisfy the requirement of high resolution.

Prior art chemically amplified positive resists also suffer from the problem known as postexposure delay (PED) that when deep-UV, electron beam or X-ray lithography is carried out, line patterns would have a T-top profile, that is, patterns become thick at the top if the leave-to-stand or delay time from exposure to postexposure baking (PEB) is extended. This problem, which arises probably because the resist surface is reduced in solubility, becomes a serious drawback on practical application. This not only makes difficult dimensional control in the lithographic process, but also adversely affects dimensional control in the processing of substrates using dry etching. In this regard, reference is made to W. Hinsberg et al., J. Photopolym. Sci. Technol., 6 (4), 535–546 (1993) and T. Kumada et al., J. Photopolym., Sci. technol., 6 (4), 571–574 (1993). There are available no chemically amplified positive resists which can solve this problem and are thus practically acceptable.

It is understood that basic compounds in the air largely participate in the PED problem associated with chemically amplified positive resists. Light exposure generates acids at the resist surface which react with basic compounds in the air and are thereby deactivated. As the delay time until PEB is extended, more amounts of acids are deactivated and accordingly, decomposition of acid labile groups are more unlikely to occur. As a consequence, an insolubilized layer is formed at the resist surface, resulting in a T-top formed pattern.

It is known from EP 558280 corresponding to JP-A 232706/1993 and EP 523957 corresponding to JP-A 249683/1993 that since addition of a basic compound suppresses the influence of basic compounds in the air, it is also effective for solving the PED problem. However, the basic compound used therein is little taken into the resist film due to volatilization, less compatible with resist components, and unevenly dispersible in a resist film over its width. Thus the basic compound cannot achieve its advantages in a reproducible manner and causes a drop of resolving power.

SUMMARY OF THE INVENTION

Therefore, an object of the present invention is to provide a chemically amplified positive resist composition having sufficiently high resolution to comply with a fine patterning technique.

We have found that a novel sulfonium salt having at least one tert-butoxycarbonylmethoxy group as an acid labile group as represented by the general formula (1) shown below can be produced by deprotecting a p-tert-butoxyphenyl sulfonium salt of the general formula (3) as disclosed in EP 615163 and EP 665220 corresponding to Japanese Patent Application Nos. 242101/1994 and 82359/1994 with a sulfonic acid of the general formula (4) to form a p-hydroxyphenyl sulfonium salt of the general formula (5), and reacting it with a tert-butyl alpha-halogenated acetate of the general formula (6) under basic conditions. This novel sulfonium salt is effective as one component to formulate a chemically amplified positive resist composition which has sufficiently high resolution to comply with a fine patterning technique. The composition is most effective when combined with deep-UV lithography.

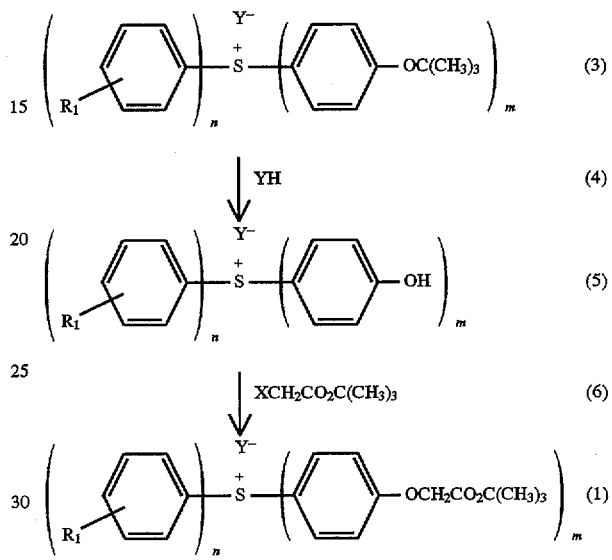

In the formulae, $R_1$ is a hydrogen atom, alkyl group or alkoxy group, X is a chlorine or bromine atom, Y is trifluoromethanesulfonate or p-toluenesulfonate, letter n is an integer of 0 to 2, m is an integer of 1 to 3, and the sum of n and m is equal to 3.

A resist composition containing a sulfonium salt of formula (1) has an enhanced dissolution rate contrast due to the effect of an acid labile group in the sulfonium salt of formula (1). There is thus provided a chemically amplified positive working resist composition having a sufficiently high resolution to lend itself to fine processing technology.

Although alkali solubility of the sulfonium salt of formula (1) itself is low, it is decomposed to generate an acid upon exposure to high energy radiation. By the action of this acid as well as postexposure baking (PEB), a tert-butyl ester is efficiently decomposed to form a carboxylic acid derivative having higher alkali solubility than phenol derivatives, which leads to an enhanced dissolution rate contrast. Therefore, the novel sulfonium salt according to the invention performs well as a photo acid generator for a chemically amplified positive working resist composition which will form a resist image having a high resolution and a wide range of focal depth.

DETAILED DESCRIPTION OF THE INVENTION

According to the present invention, a chemically amplified positive working resist composition contains a novel sulfonium salt of formula (1).

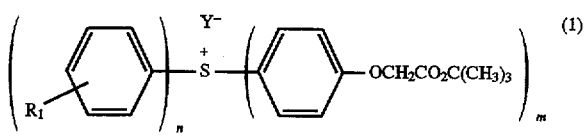

In formula (1), letter n is an integer of 0 to 2 and m is an integer of 1 to 3. They are combined to give n+m=3. $R_1$ is a hydrogen atom, alkyl group or alkoxy group. Exemplary preferred alkyl groups are those having 1 to 8 carbon atoms, including methyl, ethyl, propyl, isopropyl, n-butyl, sec-butyl, tert-butyl, hexyl, and cyclohexyl groups, with the methyl, ethyl, isopropyl, and tert-butyl groups being especially preferred. Exemplary preferred alkoxy groups are those having 1 to 8 carbon atoms, including methoxy, ethoxy, propoxy, isopropoxy, n-butoxy, sec-butoxy, tert-butoxy, hexyloxy, and cyclohexyloxy groups, with the methoxy, ethoxy, isopropoxy and tert-butoxy groups being especially preferred.

Y is trifluoromethanesulfonate or p-toluenesulfonate. More illustratively, the novel sulfonium salts of the invention are then represented by the following formula (1a) or (1b).

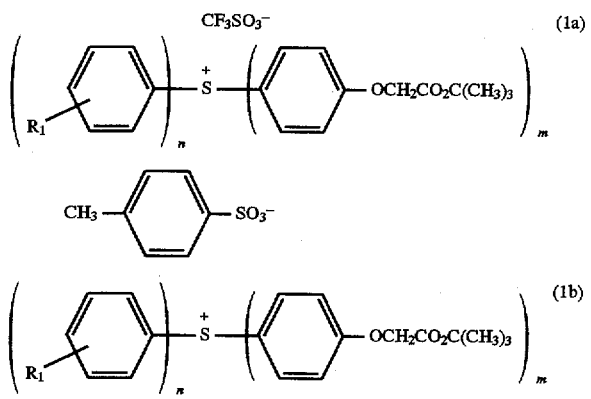

In the formulae, $R_1$, n and m are as defined above.

More particularly, use of a sulfonium salt of formula (1b) as one component of a resist composition minimizes the influence of deactivation of an acid at the resist surface by an air born basic compound, thereby restraining formation of a difficultly soluble skin layer and leading to good PED stability, which the effects are due to the p-toluenesulfonate anion. This overcomes the problem of a difficultly soluble skin layer which would otherwise cause a T-top profile, that is, the problem of PED while providing a high sensitivity.

Several illustrative, non-limiting examples of the sulfonium salt of formula (1a) include
tris(p-tert-butoxycarbonylmethoxyphenyl)sulfonium trifluoromethanesulfonate,
bis(p-tert-butoxycarbonylmethoxyphenyl)phenylsulfonium trifluoromethanesulfonate,
bis(p-tert-butoxycarbonylmethoxyphenyl)(p-methylphenyl)sulfonium trifluoromethanesulfonate,
bis(p-tert-butoxycarbonylmethoxyphenyl)(m-methylphenyl)sulfonium trifluoromethanesulfonate,
bis(p-tert-butoxycarbonylmethoxyphenyl)(o-methylphenyl)sulfonium trifluoromethanesulfonate,
bis(p-tert-butoxycarbonylmethoxyphenyl)(p-methoxyphenyl)sulfonium trifluoromethanesulfonate,
bis(p-tert-butoxycarbonylmethoxyphenyl)(m-methoxyphenyl)sulfonium trifluoromethanesulfonate,
bis(p-tert-butoxycarbonylmethoxyphenyl)(o-methoxyphenyl)sulfonium trifluoromethanesulfonate,
(p-tert-butoxycarbonylmethoxyphenyl)diphenylsulfonium trifluoromethanesulfonate,
(p-tert-butoxycarbonylmethoxyphenyl)bis(p-methylphenyl)sulfonium trifluoromethanesulfonate,
(p-tert-butoxycarbonylmethoxyphenyl)bis(m-methylphenyl)sulfonium trifluoromethanesulfonate,
(p-tert-butoxycarbonylmethoxyphenyl)bis(o-methylphenyl)sulfonium trifluoromethanesulfonate,
(p-tert-butoxycarbonylmethoxyphenyl)bis(p-methoxyphenyl)sulfonium trifluoromethanesulfonate,
(p-tert-butoxycarbonylmethoxyphenyl)bis(m-methoxyphenyl)sulfonium trifluoromethanesulfonate, and
(p-tert-butoxycarbonylmethoxyphenyl)bis(o-methoxyphenyl)sulfonium trifluoromethanesulfonate.

Several illustrative, non-limiting examples of the sulfonium salt of formula (1b) include
tris(p-tert-butoxycarbonylmethoxyphenyl)sulfonium p-toluenesulfonate,
bis(p-tert-butoxycarbonylmethoxyphenyl)phenylsulfonium p-toluenesulfonate,
bis(p-tert-butoxycarbonylmethoxyphenyl)(p-methylphenyl)sulfonium p-toluenesulfonate,
bis(p-tert-butoxycarbonylmethoxyphenyl)(m-methylphenyl)sulfonium p-toluenesulfonate,
bis(p-tert-butoxycarbonylmethoxyphenyl)(o-methylphenyl)sulfonium p-toluenesulfonate,
bis(p-tert-butoxycarbonylmethoxyphenyl)(p-methoxyphenyl)sulfonium p-toluenesulfonate,
bis(p-tert-butoxycarbonylmethoxyphenyl)(m-methoxyphenyl)sulfonium p-toluenesulfonate,
bis(p-tert-butoxycarbonylmethoxyphenyl)(o-methoxyphenyl)sulfonium p-toluenesulfonate,
(p-tert-butoxycarbonylmethoxyphenyl)diphenylsulfonium p-toluenesulfonate,
(p-tert-butoxycarbonylmethoxyphenyl)bis(p-methylphenyl)sulfonium p-toluenesulfonate, (p-tert-butoxycarbonylmethoxyphenyl)bis(m-methylphenyl)sulfonium p-toluenesulfonate,
(p-tert-butoxycarbonylmethoxyphenyl)bis(o-methylphenyl)sulfonium p-toluenesulfonate,
(p-tert-butoxycarbonylmethoxyphenyl)bis(p-methoxyphenyl)sulfonium p-toluenesulfonate,
(p-tert-butoxycarbonylmethoxyphenyl)bis(m-methoxyphenyl)sulfonium p-toluenesulfonate, and
(p-tert-butoxycarbonylmethoxyphenyl)bis(o-methoxyphenyl)sulfonium p-toluenesulfonate.

The sulfonium salt of formula (1) can be synthesized in accordance with the following route.

The process starts with a p-tert-butoxyphenyl sulfonium salt of formula (3), which is deprotected with a sulfonic acid of formula (4) corresponding to a counter anion of the sulfonium salt used, to thereby form a p-hydroxyphenyl sulfonium salt of formula (5). It is then reacted with a tert-butyl alpha-halogenated acetate of formula (6) under basic conditions, thereby synthesizing a sulfonium salt having at least one tert-butoxycarbonylmethoxy group of formula (1).

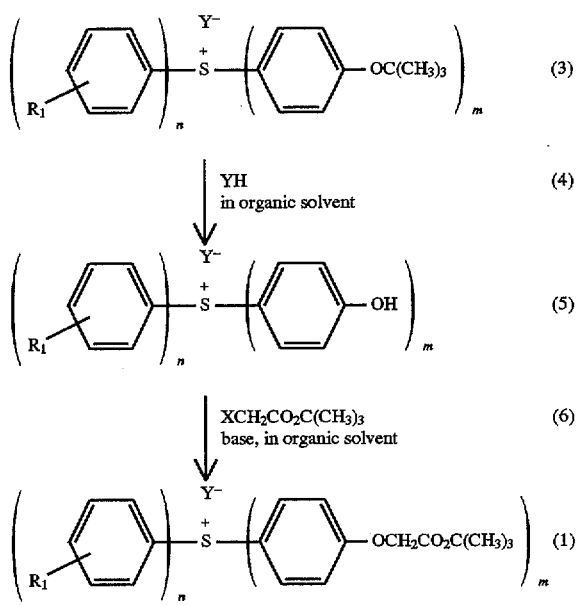

In the formulae, $R_1$ is a hydrogen atom, alkyl group or alkoxy group, X is a chlorine or bromine atom, Y is trifluoromethanesulfonate or p-toluenesulfonate, letter n is an integer of 0 to 2, m is an integer of 1 to 3, and n+m=3.

The step of deprotecting the p-tert-butoxyphenyl sulfonium salt of formula (3) is desirably carried out in an organic solvent such as methanol and ethanol. The sulfonic acid of formula (4) corresponding to a counter anion of the sulfonium salt used is added in an amount of 0.1 to 0.5 mol per mol of the sulfonium salt of formula (3). Under reflux (60° to 70° C.), reaction is desirably carried out for about 2 to 6 hours. After the completion of reaction, the solvent layer is concentrated and the residue is washed with diethyl ether to collect a p-hydroxyphenyl sulfonium salt of formula (5). The sulfonium salt of formula (5) in this crude product form can be subject to the subsequent reaction.

A tert-butoxycarbonylmethoxy group is then introduced into the sulfonium salt of formula (5) in crude product form. Desirably 1 to 2 mol of a base such as potassium carbonate and 1 to 2 mol of tert-butyl chloro- or bromoacetate of formula (6) are added per hydroxyl group of the p-hydroxyphenyl sulfonium salt of formula (5). Reaction is preferably carried out in an organic solvent such as acetone, N,N-dimethylformamide and dimethyl sulfoxide at about 60° to 90° C. for about 2 to 8 hours. After the completion of reaction, the solvent layer is washed with water and concentrated. By subsequent recrystallization or column fractionating, there is collected an end product, that is, a sulfonium salt having a tert-butoxycarbonylmethoxy group of formula (1).

It is noted that tris(hydroxyphenyl)sulfonium salts can be obtained through reaction between phenol and thionyl chloride in the presence of aluminum chloride (see S. Oae and C. Zalut, *J. Am. Chem. Soc.*, 82, 5359 (1960)); and sulfonium salts having one hydroxyl group can be obtained through acid-catalyzed condensation between diphenyl sulfoxide and phenol (see S. R. Akhtar, J. V. Crivello and J. L. Lee, *J. Org. Chem.*, 55, 4222 (1990)). However, since phenol has an active site not only at the para-position, but also at the ortho-position, there remains a possibility that an ortho-substituted isomer be produced depending on a particular reagent and catalyst used (see C. Y. Meyers and G. Picciola, *Tetrahedron Lett.*, 971 (1962)). It is then difficult to quantitatively produce a p-hydroxy compound.

In contrast, the above-mentioned process enables quantitative production of a p-hydroxy compound without forming an ortho-substituted isomer as found with phenol because the p-tert-butoxyphenylsulfonium salt is prepared using a Grignard reagent.

According to the present invention, the sulfonium salt of formula (1) is contained in a chemically amplified positive working resist composition. More particularly, the sulfonium salt may be used as a photo acid generator in a two component chemically amplified positive resist composition (alkali soluble resin/photo acid generator) or a three component chemically amplified positive resist composition (alkali soluble resin/photo acid generator/dissolution inhibitor), with the three component chemically amplified positive resist composition being preferred.

Preferably the resist composition is comprised of, in parts by weight, (A) about 150 to 700 parts, more preferably 250 to 500 parts of an organic solvent, (B) about 70 to 90 parts, more preferably 75 to 85 parts of an alkali soluble resin, (C) about 5 to 40 parts, more preferably 10 to 25 parts of a dissolution inhibitor having an acid labile group, in the case of the three component system, (D) about 1 to 15 parts, more preferably 2 to 8 parts of a sulfonium salt of formula (1), and optionally, (E) about 0.5 to 15 parts, more preferably 2 to 8 parts of another photo acid generator.

Typical embodiments of the resist composition of the invention are shown below.

Embodiment (i) is a chemically amplified positive resist composition comprising (A) an organic solvent, (B) an alkali soluble resin, (C) a dissolution inhibitor having an acid labile group, (D) a sulfonium salt of formula (1), and (E) a photo acid generator.

Embodiment (ii) is a chemically amplified positive resist composition comprising (A) an organic solvent, (B) an alkali soluble resin, (C) a dissolution inhibitor having an acid labile group, (D) a sulfonium salt of formula (1), and (E) an onium salt of the following general formula (2):

wherein $R_2$ is independently selected from substituted or unsubstituted aromatic groups, M is sulfonium or iodonium, Y is trifluoromethanesulfonate or p-toluenesulfonate, and letter n is equal to 2 or 3.

Embodiment (iii) is a chemically amplified positive resist composition comprising (A) an organic solvent, (B) an alkali soluble resin, (C) a dissolution inhibitor having an acid labile group, and (D) a sulfonium salt of formula (1).

Embodiment (iv) is a chemically amplified positive resist composition comprising (A) an organic solvent, (B) an alkali soluble resin, and (D) a sulfonium salt of formula (1).

Embodiment (v) is a chemically amplified positive resist composition comprising (A) an organic solvent,
(B) an alkali soluble resin,
(D) a sulfonium salt of formula (1), and
(E) a photo acid generator.

Examples of organic solvent (A) include ketones such as cyclohexanone and methyl-2-n-amylketone; alcohols such as 3-methoxybutanol, 3-methyl-3-methoxybutanol, 1-methoxy-2-propanol and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; and esters such as propylene glycol monomethyl ether acetate, propylene glycol monoethyl ether acetate, ethyl lactate, ethyl pyruvate, butyl acetate, methyl 3-methoxypropionate and ethyl 3-ethoxypropionate, alone or in admixture of two or more. The most preferred solvent is 1-ethoxy-2-propanol because the photo acid generator of the resist composition is most soluble therein.

Examples of alkali soluble resin (B) include polyhydroxystyrene and derivatives thereof. Preferred are those polyhydroxystyrene derivatives wherein hydrogen atoms of some OH groups of polyhydroxystyrene are replaced by acid labile groups and hydroxystyrene copolymers. In the former, examples of the acid labile group used therein include tert-butyl, tert-butoxycarbonyl, tetrahydropyranyl, methoxymethyl, trimethylsilyl, and tert-butyldimethylsilyl groups, with the tert-butyl, tert-butoxycarbonyl, and tetrahydropyranyl groups being preferred. Included in the latter are copolymers of hydroxystyrene and styrene, copolymers of hydroxystyrene and tert-butyl acrylate, copolymers of hydroxystyrene and tert-butyl methacrylate, copolymers of hydroxystyrene and maleic anhydride, and copolymers of hydroxystyrene and di-tert-butyl maleate. The polyhydroxystyrene and derivatives thereof should preferably have a weight average molecular weight of about 5,000 to about 100,000.

Dissolution inhibitor (C) should have at least one group which is decomposable with an acid (acid labile group) in a molecule and may be either a low molecular weight compound or a polymer. Any of well-known dissolution inhibitors may be used. Exemplary low molecular weight compounds include bisphenol A derivatives having an acid labile group and carbonate derivatives having an acid labile group, with those bisphenol A derivatives wherein OH groups of bisphenol A are replaced by tert-butoxy or butoxycarbonyloxy groups being preferred. Examples of the polymeric dissolution inhibitor include copolymers of p-butoxystyrene and tert-butyl acrylate, and copolymers of p-butoxystyrene and maleic anhydride, with those copolymers having a weight average molecular weight of about 500 to about 10,000 being preferred.

Examples of photo acid generator (E) include onium salts, oxime sulfonic acid derivatives, 2,6-dinitrobenzylsulfonic acid derivatives, diazonaphthoquinone sulfonate derivatives, 2,4-bistrichloromethyl-6-aryl-1,3,5-triazine derivatives, and α,α'-bisarylsulfonyl diazomethane derivatives. Preferred are onium salts of the following general formula (2):

$$(R_2)_nMY \quad (2)$$

wherein $R_2$ is independently selected from substituted or unsubstituted aromatic groups, M is sulfonium or iodonium, Y is p-toluenesulfonate or trifluoromethanesulfonate, and letter n is equal to 2 or 3. Exemplary aromatic groups represented by $R_2$ are a phenyl group and phenyl groups having an alkyl or alkoxy substituent as described in formula (1).

Illustrative examples of the onium salt are given by the following iodonium and sulfonium salts.

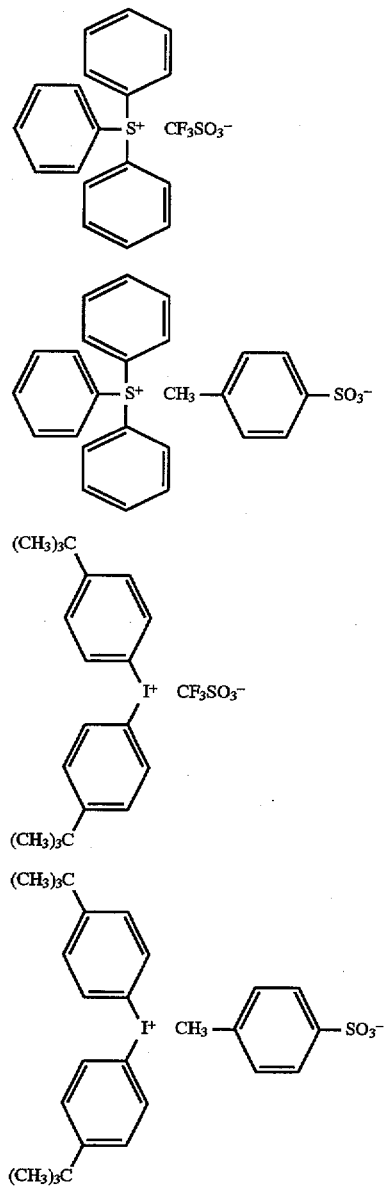

The resist composition of the invention may further contain various additives, for example, a nitrogenous compound for improving PED stability, a surface-active agent for facilitating coating, and a light-absorbing agent for reducing irregular reflection from the substrate.

Typical nitrogenous compounds are amine and amide compounds having a boiling point of 150° C. or higher. Examples include aniline, N-methylaniline, N,N-dimethylaniline, o-toluidine, m-toluidine, p-toluidine, 2,4-lutidine, quinoline, isoquinoline, formamide, N-methylformamide, N,N-dimethylformamide, acetamide, N-methylacetamide, N,N-dimethylacetamide, 2-pyrrolidone, N-methylpyrrolidone, imidazole, α-picoline, β-picoline, γ-picoline, o-aminobenzoic acid, m-aminobenzoic acid, p-aminobenzoic acid, 1,2-phenylenediamine, 1,3- phenylenediamine, 1,4-phenylenediamine, 2-quinolinecarboxylic acid, 2-amino-4-nitrophenol, and triazines such as 2-(p-chlorophenyl)-4,6-trichloromethyl-s-triazine. Preferred among others are pyrrolidone, N-methylpyrrolidone, o-, m- and p-aminobenzoic acid, 1,2-, 1,3- and 1,4-phenylenediamine.

Examples of the surfactant include perfluoroalkylpolyoxyethylene ethanols, fluorinated alkyl esters, perfluoroalkylamine oxides, and perfluoroalkyl EO addition products.

Examples of the light-absorbing agent include diaryl sulfoxides, diaryl sulfones, 9,10-dimethylanthracene, and 9-fluorenone.

With respect to the use of the resist composition of the invention and light exposure, any of well-known lithography techniques may be used. The resist composition of the invention is best suited for fine patterning using deep UV light of 254 to 193 nm and electron beam.

There has been described a resist composition containing a novel sulfonium salt of formula (1) which affords an enhanced dissolution rate contrast between exposed and unexposed areas due to the inclusion of at least one tert-butoxycarbonylmethoxy group which is an acid labile group. The resist composition containing a novel sulfonium salt is sensitive to high energy radiation such as deep UV line, electron beam and X-ray, especially KrF excimer laser beams as a positive resist material, can be patterned by development with alkaline aqueous solution, and has high sensitivity, resolution and resistance to plasma etching with the resulting resist pattern having improved heat resistance.

EXAMPLE

Examples of the present invention are given below by way of illustration and not by way of limitation. The synthesis of novel sulfonium salts is described prior to Examples and Comparative Examples.

Synthesis Example 1

Synthesis of (p-hydroxyphenyl)diphenylsulfonium trifluoromethanesulfonate

A solution of 48.4 g (0.1 mol) of (p-tert-butoxyphenyl)diphenylsulfonium trifluoromethanesulfonate and 1.5 g (0.01 mol) of trifluoromethanesulfonic acid in 500 g of methanol was heated at 60° to 70° C. for 6 hours with stirring. The reaction mixture was evaporated in vacuo. The residual oil was washed two times with 100 g of diethyl ether. The amount of this crude product was 40 g (yield 93%). Without further purification, the crude product was used in subsequent reaction.

Synthesis of (p-tert-butoxycarbonylmethoxyphenyl)diphenylsulfonium trifluoromethanesulfonate A solution of 40 g of crude product (described above), 20.7 g (0.15 mol) of anhydrous potassium carbonate, and 18.1 g (0.12 mol) of tert-butyl chloroacetate in 400 g of acetone was heated at 60° C. for 3 hours with stirring (potassium carbonate was suspended). After cooling, the inorganic salts were filtered off and the filtrate was evaporated in vacuo. The residue was purified by silica gel column chromatography using chloroform-methanol (10:1) as the eluting solvent, to give 46.1 g (85% yield in two steps) of (p-tert-butoxycarbonylmethoxyphenyl)diphenylsulfonium trifluoromethanesulfonate (99% purity).

The analytical data (NMR spectroscopy, IR spectroscopy, and elemental analysis) were shown below.

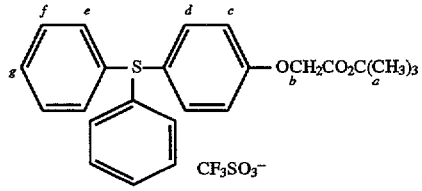

| | | | |
|---|---|---|---|
| (a) | 1.46 | singlet | 9H |
| (b) | 4.61 | singlet | 2H |
| (c) | 7.14–7.18 | doublet | 2H |
| (d)–(g) | 7.65–7.74 | multiplet | 12H |

IR: (cm$^{-1}$)

3093, 3066, 2981, 2935, 2881, 1745, 1589, 1497, 1477, 1446, 1417, 1396, 1371, 1319, 1265, 1224, 1155, 1070, 1068, 1066, 1030, 997, 943, 836, 752, 684, 638 elemental analysis for $C_{25}H_{25}O_6S_2F_3$ Calcd. (%) C: 55.3 H: 4.6 Found (%) C: 55.2 H: 4.7

Synthesis Example 2

Synthesis of bis(p-hydroxyphenyl)phenylsulfonium trifluoromethanesulfonate

A solution of 55.7 g (0.1 mol) of bis(p-tert-butoxyphenyl)phenylsulfonium trifluoromethanesulfonate and 1.5 g (0.01 mol) of trifluoromethanesulfonic acid in 500 g of methanol was heated at 60° to 70° C. for 7 hours with stirring. The reaction mixture was evaporated in vacuo. The residual oil was washed two times with 100 g of diethyl ether. The amount of this crude product was 42 g (94% yield). Without further purification, the crude product was used in subsequent reaction.

Synthesis of bis(p-tert-butoxycarbonylmethoxyphenyl) phenylsulfonium trifluoromethanesulfonate A solution of 42 g of crude product (described above), 41.5 g (0.30 mol) of anhydrous potassium carbonate, and 36.2 g (0.24 mol) of tert-butyl chloroacetate in 300 g of dimethyl sulfoxide was heated at 80° C. for 2 hours with stirring (potassium carbonate was suspended). After cooling, reaction mixture was poured onto 300 g of water and organic layer was extracted with 300 g of chloroform. The extract was washed two times with 300 g of water and then evaporated in vacuo. The residue was purified by silica gel column chromatography using chloroform-methanol (10:1) as the eluting solvent, to give 55.1 g (82% yield in two steps) of bis(p-tert-butoxycarbonylmethoxyphenyl)phenylsulfonium trifluoromethanesulfonate (99% purity).

The analytical data (NMR spectroscopy, IR spectroscopy, and elemental analysis) were shown below.

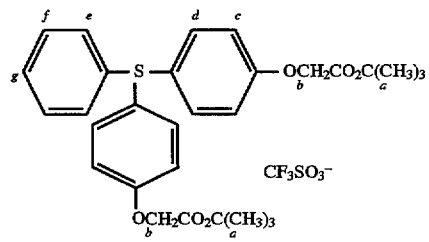

| | | | |
|---|---|---|---|
| (a) | 1.45 | singlet | 18H |
| (b) | 4.60 | singlet | 4H |

¹H-NMR: CDCl₃, δ (ppm)

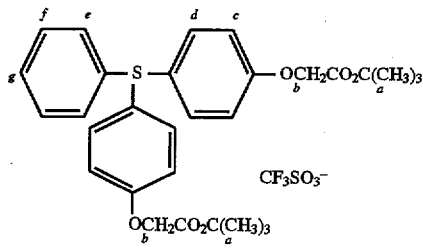

| (c)      | 7.13–7.17 | doublet   | 4H |
| (d)–(g)  | 7.64–7.74 | multiplet | 9H |

IR: (cm⁻¹)

3093, 3066, 2982, 2935, 2881, 1745, 1589, 1497, 1477,
1446, 1418, 1396, 1372, 1319, 1265, 1225, 1155, 1070, 1068,
1065, 1030, 997, 942, 836, 752, 684, 638

Elemental analysis for $C_{31}H_{35}O_9S_2F_3$ Calcd. (%) C: 55.4 H: 5.2 Found (%) C: 55.1 H: 5.3

Synthesis Example 3

Synthesis of bis(p-hydroxyphenyl)(p-methylphenyl) sulfonium trifluoromethanesulfonate A solution of 28.5 g (0.05 mol) of bis(p-tert-butoxyphenyl)(p-methylphenyl)sulfonium trifluoromethanesulfonate and 1.5 g (0.01 mol) of trifluoromethanesulfonic acid in 400 g of methanol was heated at 60° to 70° C. for 6.5 hours with stirring. The reaction mixture was evaporated in vacuo. The residual oil was washed two times with 200 g of diethyl ether. The amount of this crude product was 22 g (96% yield). Without further purification, the crude product was used in subsequent reaction.

Synthesis of bis(p-tert-butoxycarbonylmethoxyphenyl)(p-methylphenyl)sulfonium trifluoromethanesulfonate A solution of 22 g of crude product (described above), 20.7 g (0.15 mol) of anhydrous potassium carbonate, and 22.6 g (0.15 mol) of tert-butyl chloroacetate in 150 g of N,N-dimethylformamide was heated at 80° C. for 3 hours with stirring (potassium carbonate was suspended). After cooling, reaction mixture was poured onto 200 g of water and organic layer was extracted with 200 g of chloroform. The extract was washed two times with 200 g of water and then evaporated in vacuo. The residue was purified by silica gel column chromatography using chloroform-methanol (10:1) as the eluting solvent, to give 29.0 g (84% yield in two steps) of bis(p-tert-butoxycarbonylmethoxyphenyl)(p-methylphenyl)sulfonium trifluoromethanesulfonate (99 % purity).

The analytical data (NMR spectroscopy, IR spectroscopy, and elemental analysis) were shown below.

¹H-NMR: CDCl₃, δ (ppm)

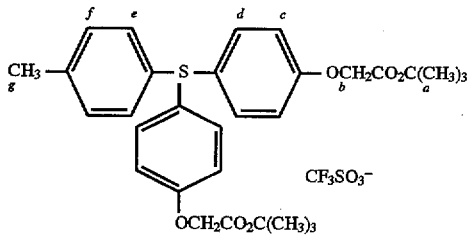

| (a)     | 14.1      | singlet   | 18H |
| (b)     | 4.60      | singlet   | 4H  |
| (c)     | 7.13–7.17 | doublet   | 4H  |
| (d)–(f) | 7.64–7.74 | multiplet | 8H  |
| (g)     | 2.43      | singlet   | 3H  |

IR: (cm⁻¹)

3093, 3066, 2981, 2935, 2881, 1746, 1589, 1497, 1477,
1446, 1417, 1394, 1371, 1319, 1265, 1224, 1157, 1071, 1068,
1066, 1032, 997, 945, 836, 752, 685, 638

Elemental analysis for $C_{32}H_{37}O_9S_2F_3$ Calcd. (%) C: 56.0 H: 5.4 Found (%) C: 55.6 H: 5.3

Synthesis Example 4

Synthesis of tris(p-hydroxyhexyl)sulfonium trifluoromethanesulfonate

A solution of 100.0 g (0.16 mol) of tris(p-tert-butoxyphenyl)sulfonium trifluoromethanesulfonate and 2.4 g (0.016 mol) of trifluoromethanesulfonic acid in 320 g of ethanol was heated at 70° to 80° C. for 7 hours with stirring. The reaction mixture was evaporated in vacuo. The residual oil was washed two times with 150 g of diethyl ether. The amount of this crude product was 68 g (92% yield). Without further purification, the crude product was used in subsequent reaction.

Synthesis of tris(p-tert-butoxycarbonylmethoxyphenyl) sulfonium trifluoromethanesulfonate A solution of 68 g of crude product (described above), 110.8 g (0.80 mol) of anhydrous potassium carbonate, and 120.5 g (0.80 mol) of tert-butyl chloroacetate in 320 g of N,N-dimethylformamide was heated at 80° C. for 2 hours with stirring (potassium carbonate was suspended). After cooling, reaction mixture was poured onto 300 g of water and organic layer was extracted with 300 g of chloroform. The extract was washed two times with 300 g of water and then evaporated in vacuo. The residue was purified by silica gel column chromatography using chloroform-methanol (10:1) as the eluting solvent, to give 108.0 g (84% yield in two steps) of bis(p-tert-butoxycarbonylmethoxyphenyl) phenylsulfonium trifluoromethanesulfonate with 98% purity.

The analytical data (NMR spectroscopy, IR spectroscopy, and elemental analysis) were shown below.

¹H-NMR: CDCl₃, δ (ppm)

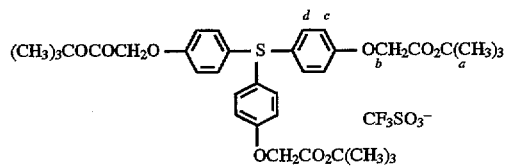

| (a) | 1.45 | singlet | 27H |
|---|---|---|---|
| (b) | 4.56 | singlet | 6H |
| (c) | 7.10–7.13 | doublet | 6H |
| (d)–(g) | 7.57–7.60 | doublet | 6H |

IR: (cm⁻¹)

3097, 2981, 2937, 1747, 1589, 1494, 1446, 1417, 1371, 1317, 1263, 1226, 1157, 1076, 1031, 944, 833, 752, 638

Elemental analysis for $C_{37}H_{45}O_{12}S_2F_3$ Calcd. (%) C: 55.4 H: 5.7 Found (%) C: 55.2 H: 5.6

Synthesis Example 5

Synthesis of bis(p-hydroxyphenyl)phenylsulfonium p-toluenesulfonate

A solution of 5.8 g (0.01 mol) of bis(p-tert-butoxyphenyl) phenylsulfonium p-toluenesulfonate and 0.95 g (0.005 mol) of p-toluenesulfonic acid in 35 g of methanol was heated at 60° C. for 5 hours with stirring. The reaction mixture was evaporated in vacuo. The residual oil was washed two times with 200 g of diethyl ether. The amount of this crude product was 4.7 g (100% yield). Without further purification, the crude product was used in subsequent reaction.

Synthesis of bis(p-tert-butoxycarbonylmethoxyphenyl) sulfonium p-toluenesulfonate A solution of 4.7 g of crude product (described above), 4.1 g (0.03 mol) of anhydrous potassium carbonate, and 3.6 g (0.024 mol) of tert-butyl chloroacetate in 50 g of dimethyl sulfoxide was heated at 80° C. for 2 hours with stirring (potassium carbonate was suspended). After cooling, reaction mixture was poured onto 100 g of water and organic layer was extracted with 100 g of chloroform. The extract was washed two times with 100 g of water and then evaporated in vacuo. The residue was purified by silica gel column chromatography using chloroform-methanol (10:1) as the eluting solvent, to give 5.6 g (80% yield in two steps) of bis(p-tert-butoxycarbonylmethoxyphenyl) phenylsulfonium p-toluenesulfonate with 97% purity.

The analytical data (NMR spectroscopy, IR spectroscopy, and elemental analysis) were shown below.

¹H-NMR: CDCl₃, δ (ppm)

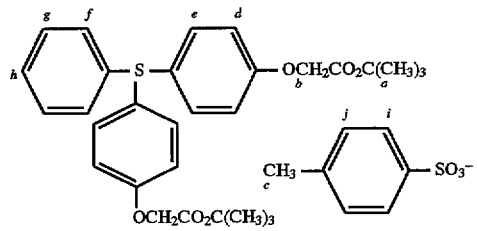

| (a) | 1.43 | singlet | 18H |
|---|---|---|---|
| (b) | 4.56 | singlet | 4H |
| (c) | 2.26 | singlet | 3H |
| (d) | 7.11–7.14 | doublet | 4H |
| (e)–(h) | 7.52–7.70 | multiplet | 9H |

¹H-NMR: CDCl₃, δ (ppm)

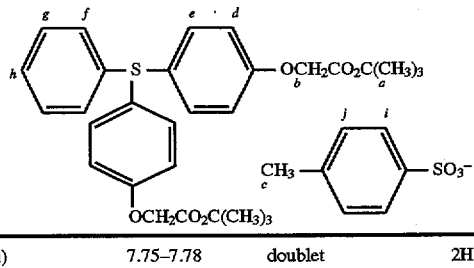

| (i) | 7.75–7.78 | doublet | 2H |
|---|---|---|---|
| (j) | 6.99–7.02 | doublet | 2H |

IR: (cm⁻¹)

3059, 2979, 2933, 1746, 1583, 1489, 1446, 1394, 1308, 1266, 1204, 1202, 1159, 1119, 1076, 1027, 1033, 1012, 928, 895, 843, 826

Elemental analysis for $C_{37}H_{42}O_9S_2$ Calcd. (%) C: 64.0 H: 6.1 Found (%) C: 63.8 H: 6.0

Synthesis Example 6

Synthesis of tris(p-hydroxyphenyl)sulfonium p-toluenesulfonate

A solution of 6.5 g (0.01 mol) of tris(p-tert-butoxyphenyl) sulfonium p-toluenesulfonate and 0.95 g (0.005 mol) of p-toluenesulfonic acid in 40 g of methanol was heated at 60° C. for 7 hours with stirring. The reaction mixture was evaporated in vacuo. The residual oil was washed two times with 200 g of diethyl ether. The amount of this crude product was 4.7 g (97% yield). Without further purification, the crude product was used in subsequent reaction.

Synthesis of tris(p-tert-butoxycarbonylmethoxyphenyl) sulfonium p-toluenesulfonate A solution of 4.7 g of crude product (described above), 6.9 g (0.05 mol) of anhydrous potassium carbonate, and 7.5 g (0.05 mol) of tert-butyl chloroacetate in 60 g of dimethyl sulfoxide was heated at 80° C. for 3 hours with stirring (potassium carbonate was suspended). After cooling, reaction mixture was poured onto 100 g of water and organic layer was extracted with 100 g of chloroform. The extract was washed two times with 100 g of water and then evaporated in vacuo. The residue was purified by silica gel column chromatography using chloroform-methanol (10:1) as the eluting solvent, to give 7.0 g (85% yield in two steps) of tris(p-tert-butoxycarbonylmethoxyphenyl)sulfonium p-toluenesulfonate with 97% purity.

The analytical data (NMR spectroscopy, IR spectroscopy, and elemental analysis) were shown below.

¹H-NMR: CDCl₃, δ (ppm)

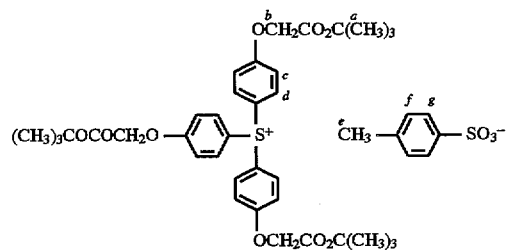

| (a) | 1.41 | singlet | 27H |
|---|---|---|---|
| (b) | 4.56 | singlet | 6H |

-continued

¹H-NMR: CDCl₃, δ (ppm)

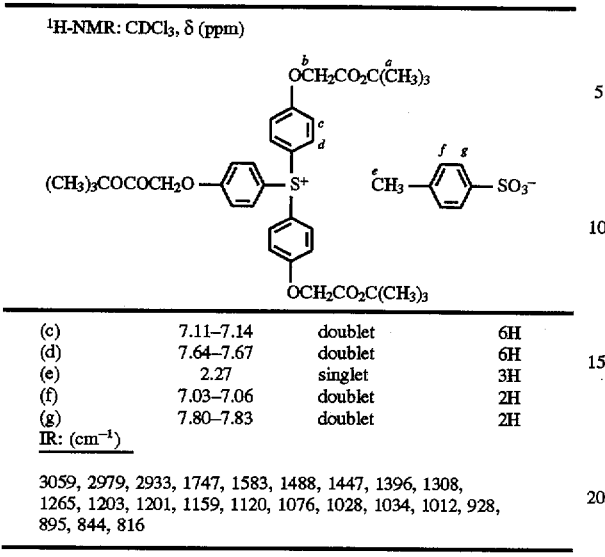

| (c) | 7.11–7.14 | doublet | 6H |
| (d) | 7.64–7.67 | doublet | 6H |
| (e) | 2.27 | singlet | 3H |
| (f) | 7.03–7.06 | doublet | 2H |
| (g) | 7.80–7.83 | doublet | 2H |

IR: (cm⁻¹)

3059, 2979, 2933, 1747, 1583, 1488, 1447, 1396, 1308, 1265, 1203, 1201, 1159, 1120, 1076, 1028, 1034, 1012, 928, 895, 844, 816

Elemental analysis for $C_{43}H_{52}O_{12}S_2$ Calcd. (%) C: 62.6 H: 6.4 Found (%) C: 62.9 H: 6.2

Examples 1–14 & Comparative Examples 1–4

Liquid resist compositions were prepared by dissolving a polyhydroxystyrene, a photo acid generator, and a dissolution inhibitor in 1-ethoxy-2-propanol (abbreviated as EtOIPA) in accordance with the formulation shown in Table 1. The polyhydroxystyrene was selected from a polyhydroxystyrene derivative of the following formula Polym. 1 wherein some OH groups are protected by t-butoxy, carbonyl groups, a polyhydroxystyrene derivative of the following formula Polym. 2 wherein some OH groups are protected by t-butyl groups, and a polyhydroxystyrene derivative of the following formula Polym. 3 wherein some OH groups are protected by tetrahydropyranyl groups. The photo acid generator was selected from the onium salts of the formulae PAG. 1 to PAG. 5. The dissolution inhibitor was 2,2'-bis(4-tert-butoxycarbonyloxyphenyl)propane of the formula DRI.1.

Each of the compositions was passed through a 0.2-μm Teflon® filter. It was then spin coated onto a silicon wafer to form a coating. of 0.8 μm thick. With the silicon wafer rested on a hot plate at 100° C., the coating was prebaked for 120 seconds.

The film was exposed to a pattern of light by means of an excimer laser stepper model NSR 2005EX (manufactured by Nikon K.K., numerical aperture NA=0.5), baked at 90° C. for 60 seconds, and developed with an aqueous solution of 2.38% tetramethylammonium hydroxide, obtaining a positive pattern.

The resulting resist patterns were evaluated as follows.

First, sensitivity (Eth value) was determined. Provided that the exposure dose with which the top and bottom of a 0.35-μm line-and-space pattern were resolved at 1:10 was the optimum exposure (sensitivity Eop), the minimum line width of a line-and-space pattern which was recognized separate at this exposure was the resolution of a test resist. The configuration of the resist pattern resolved was observed under a scanning electron microscope.

The results are shown in Table 1.

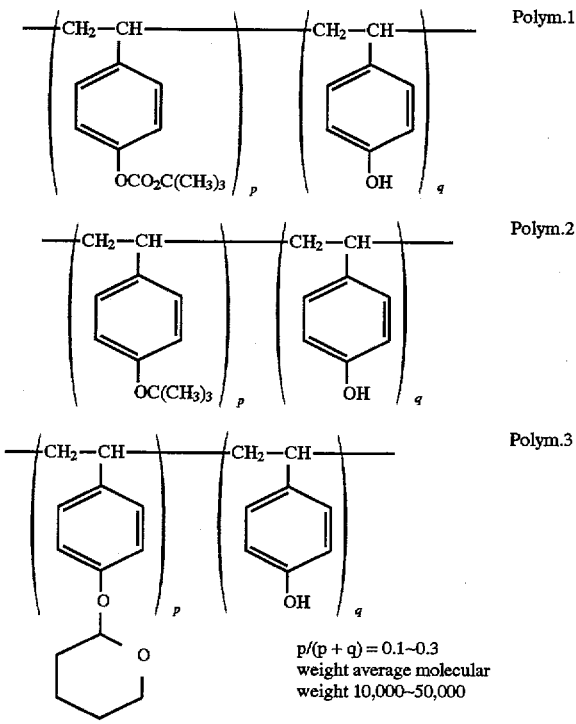

p/(p + q) = 0.1–0.3
weight average molecular weight 10,000–50,000

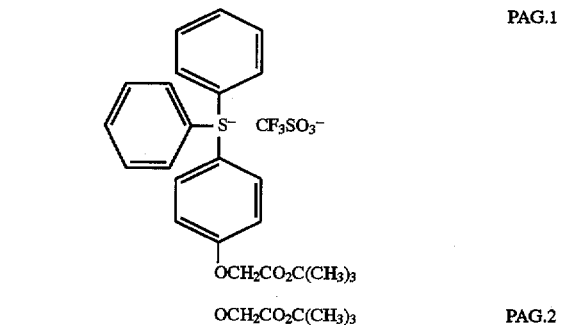

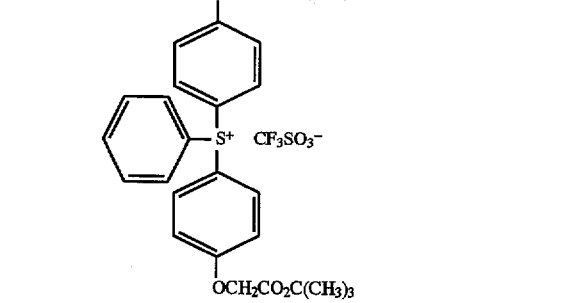

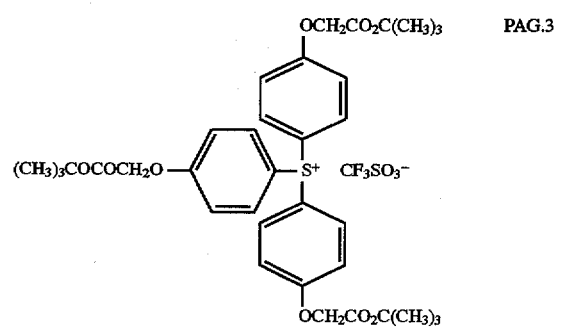

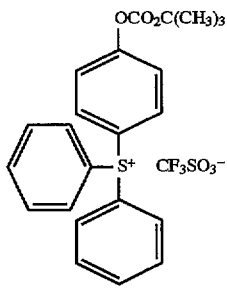

PAG.4

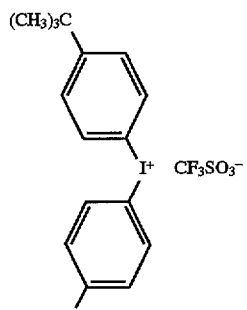

PAG.5

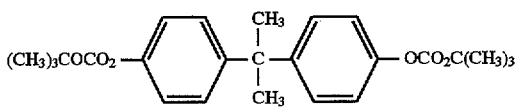

DRI.1

Examples 15–28 and Comparative Examples 5–8

Liquid resist compositions were prepared as in Example 1 except that the photo acid generator was selected from the onium salts of the formulae PAG. 6 to PAG. 8 as well as PAG. 4 and PAG. 5. Positive resist patterns were similarly obtained therefrom and evaluated as follows.

First, sensitivity (Eth value) was determined. Provided that the exposure dose with which the top and bottom of a 0.35-μm line-and-space pattern were resolved at 1:1 was the optimum exposure (sensitivity Eop), the minimum line width of a line-and-space pattern which was recognized separate at this exposure was the resolution of a test resist. The configuration of the resist pattern resolved was observed under a scanning electron microscope. The resist was determined for PED stability by exposing at the optimum exposure, leaving the resist film to stand for a varying time, and baking the film. The delay time was determined at which a change in the resist pattern configuration was observed, for example, the line pattern was T-top formed or resolution became impossible. The longer the delay time, the better is the PED stability.

The results are shown in Table 2.

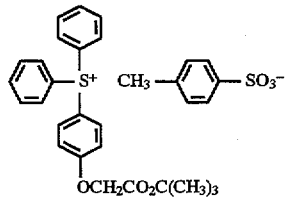

PAG.6

TABLE 1

| Example | Resist composition (pbw) ||||  Sensitivity Eop (mJ/cm$^2$) | Resolution (μm) | Pattern profile |
| | Alkali soluble resin | Photo Acid generator | Dissolution inhibitor | Solvent | | | |
|---|---|---|---|---|---|---|---|
| E1 | Polym.1 (75) | PAG.1 (5) | DRI.1 (20) | EtOIPA (450) | 4.0 | 0.24 | rectangular |
| E2 | Polym.1 (75) | PAG.2 (5) | DRI.1 (20) | EtOIPA (450) | 4.5 | 0.24 | rectangular |
| E3 | Polym.1 (75) | PAG.3 (5) | DRI.1 (20) | EtOIPA (450) | 5.5 | 0.22 | rectangular |
| E4 | Polym.1 (70) | PAG.1 (2) PAG.4 (2) | DRI.1 (20) | EtOIPA (450) | 4.0 | 0.26 | rectangular |
| E5 | Polym.1 (70) | PAG.3 (2) PAG.5 (2) | DRI.1 (20) | EtOIPA (450) | 5.0 | 0.26 | rectangular |
| E6 | Polym.1 (75) | PAG.3 (6) | — | EtOIPA (450) | 5.5 | 0.26 | rectangular |
| E7 | Polym.1 (75) | PAG.3 (3) PAG.5 (2) | — | EtOIPA (450) | 5.5 | 0.30 | rectangular |
| E8 | Polym.2 (75) | PAG.1 (5) | DRI.1 (20) | EtOIPA (450) | 3.5 | 0.24 | rectangular |
| E9 | Polym.2 (75) | PAG.3 (5) | DRI.1 (20) | EtOIPA (450) | 5.0 | 0.24 | rectangular |
| E10 | Polym.2 (70) | PAG.2 (5) PAG.5 (2) | DRI.1 (20) | EtOIPA (450) | 4.5 | 0.28 | rectangular |
| E11 | Polym.2 (75) | PAG.3 (5) | — | EtOIPA (400) | 5.0 | 0.30 | rectangular |
| E12 | Polym.3 (75) | PAG.1 (5) | DRI.1 (20) | EtOIPA (450) | 5.0 | 0.26 | rectangular |
| E13 | Polym.3 (75) | PAG.3 (5) | DRI.1 (20) | EtOIPA (450) | 5.5 | 0.24 | rectangular |
| E14 | Polym.3 (75) | PAG.2 (2) PAG.5 (2) | DRI.1 (20) | EtOIPA (400) | 5.5 | 0.28 | rectangular |
| CE1 | Polym.1 (75) | PAG.4 (5) | DRI.1 (20) | EtOIPA (450) | 4.0 | 0.28 | somewhat forward taper |
| CE2 | Polym.2 (75) | PAG.5 (5) | DRI.1 (20) | EtOIPA (450) | 4.0 | 0.30 | somewhat forward taper |
| CE3 | Polym.3 (75) | PAG.5 (5) | DRI.1 (20) | EtOIPA (450) | 4.0 | 0.30 | forward taper |
| CE4 | Polym.1 (80) | PAG.4 (6) | — | EtOIPA (400) | 5.0 | 0.30 | forward taper |

*EtOIPA: 1-ethoxy-2-propanol

-continued

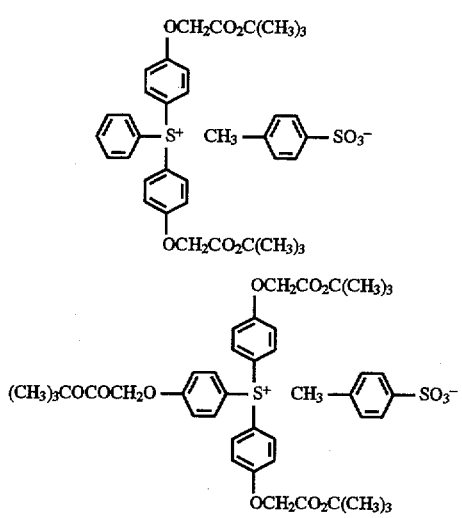

PAG.7

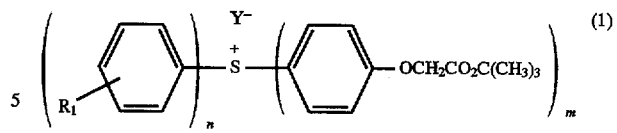

wherein $R_1$ is a hydrogen atom, alkyl group or alkoxy group, Y is trifluoromethanesulfonate or p-toluenesulfonate, n is an integer of 0 to 2, m is an integer of 1 to 3, and the sum of n and m is equal to 3.

2. A chemically amplified positive resist composition according to claim 1, comprising an admixture of (A) an organic solvent, (B) an alkali soluble resin, (C) a dissolution inhibitor having an acid labile group, (D) a sulfonium salt of formula (1), and (E) a photo acid generator.

3. A chemically amplified positive resist composition according to claim 1 comprising an admixture of (A) an organic solvent,

TABLE 2

| Example | Resist composition (pbw) | | | | Sensitivity Eop (mJ/cm²) | Resolution (μm) | Pattern profile | PED stavility (min.) |
|---|---|---|---|---|---|---|---|---|
| | Alkali soluble resin | Photo Acid generator | Dissolution inhibitor | Solvent | | | | |
| E15 | Polym.1 (80) | PAG.6 (5) | DRI.1 (20) | EtOIPA (450) | 13.0 | 0.24 | rectangular | ≧60 |
| E16 | Polym.1 (80) | PAG.7 (5) | DRI.1 (20) | EtOIPA (450) | 15.0 | 0.24 | rectangular | ≧60 |
| E17 | Polym.1 (80) | PAG.8 (5) | DRI.1 (20) | EtOIPA (450) | 18.0 | 0.22 | rectangular | ≧60 |
| E18 | Polym.1 (75) | PAG.6 (2) PAG.4 (2) | DR1.1 (20) | EtOIPA (500) | 11.0 | 0.28 | rectangular | ≧30 |
| E19 | Polym.1 (75) | PAG.8 (5) | — | EtOIPA (500) | 19.0 | 0.24 | rectangular | ≧60 |
| E20 | Polym.1 (75) | PAG.7 (2) PAG.5 (2) | — | EtOIPA (500) | 12.0 | 0.28 | rectangular | ≧30 |
| E21 | Polym.2 (70) | PAG.6 (5) | DRL1 (20) | EtOIPA (450) | 12.0 | 0.25 | rectangular | ≧30 |
| E22 | Polym.2 (70) | PAG.8 (5) | DRL1 (20) | EtOIPA (450) | 16.0 | 0.25 | rectangular | ≧30 |
| E23 | Polym.2 (70) | PAG.8 (3) PAC.4 (2) | DRI.1 (10) | EtOIPA (400) | 14.0 | 0.28 | rectangular | ≧30 |
| E24 | Polym.2 (75) | PAG.8 (5) | — | EtOIPA (450) | 18.0 | 0.25 | rectangular | ≧30 |
| E25 | Polym.3 (70) | PAG.8 (5) | DRL1 (20) | EtOIPA (450) | 18.0 | 0.26 | rectangular | ≧30 |
| E26 | Polym.3 (70) | PAG.6 (3) PAG.4 (2) | DRL1 (10) | EtOIPA (400) | 16.0 | 0.30 | rectangular | ≧30 |
| E27 | Polym.3 (75) | PAG.8 (5) | — | EtOIPA (450) | 20.0 | 0.28 | rectangular | ≧30 |
| E28 | Polym.1 (80) | PAG.8 (5) | DRL1 (20) | EtOIPA (400) [NMP (0.1)] | 26.0 | 0.22 | rectangular | ≧90 |
| CE5 | Polym.1 (75) | PAG.4 (5) | DRI-1 (20) | EtOIPA (450) | 4.0 | 0.28 | somewhat forward taper | ≧5 |
| CE6 | Polym.2 (75) | PAG.5 (5) | DRL1 (20) | EtOIPA (450) | 4.0 | 0.30 | somewhat forward taper | ≧5 |
| CE7 | Polym.3 (75) | PAG.5 (5) | DRT.1 (20) | EtOIPA (450) | 4.0 | 0.30 | forward taper | ≧5 |
| CE8 | Polym.1 (80) | PAG.4 (6) | — | EtOIPA (400) | 5.0 | 0.30 | forward taper | ≧5 |

EtOIPA: 1-ethoxy-2-propanol, NMP: N-methylpyrrolidone

Japanese Patent Application No. 329914/1994 is incorporated herein by reference.

Although some preferred embodiments have been described, many modifications and variations may be made thereto in the light of the above teachings. It is therefore to be understood that within the scope of the appended claims, the invention may be practiced otherwise than as specifically described.

We claim:

1. In a chemically amplified positive resist composition, the improvement wherein said composition comprises a sulfonium salt of formula (1):

(B) an alkali soluble resin, (C) a dissolution inhibitor having an acid labile group, (D) a sulfonium salt of formula (1), and (E) an onium salt of the following general formula (2):

$$(R_2)_n MY \quad (2)$$

wherein $R_2$ is independently a substituted or unsubstituted aromatic group, M is sulfonium or iodonium, Y is trifluoromethanesulfonate or p-toluenesulfonate, and n is equal to 2 or 3.

4. A chemically amplified positive resist composition according to claim 1, comprising an admixture of (A) an organic solvent, (B) an alkali soluble resin, (C) a dissolution inhibitor having an acid labile group, (D) a sulfonium salt of formula (1).

5. A chemically amplified positive resist composition according to claim 1, comprising an admixture of (A) an organic solvent, (B) an alkali soluble resin, and (D) a sulfonium salt of formula (1).

6. A chemically amplified positive resist composition comprising (A) an organic solvent, (B) an alkali soluble resin, (D) a sulfonium salt of formula (1) as set forth in claim 1, and (E) a photo acid generator.

7. The composition of claim 2 wherein said alkali soluble resin (B) is a polyhydroxystyrene in which hydrogen atoms of some hydroxyl groups are replaced by acid labile groups and which has a weight average molecular weight of about 5,000 to about 100,000.

8. A chemically amplified positive resist composition according to claim 1, wherein $R_1$ is $C_{1-8}$-alkyl or $C_{1-8}$-alkoxy.

9. A chemically amplified positive resist composition according to claim 1, wherein $R_1$ is methyl, ethyl, propyl, isopropyl, n-butyl, sec-butyl, tert-butyl, hexyl, cyclohexyl, methoxy, ethoxy, propoxy, isopropoxy n-butoxy, sec-butoxy, tert-butoxy, hexyloxy, or cyclohexyloxy.

10. A chemically amplified positive resist composition according to claim 1, wherein the sulfonium salt is
tris(p-tert-butoxycarbonylmethoxyphenyl)sulfonium trifluoromethanesulfonate,
bis(p-tert-butoxycarbonylmethoxyphenyl)phenylsulfonium trifluoromethanesulfonate,
bis(p-tert-butoxycarbonylmethoxyphenyl)(p-methylphenyl)sulfonium trifluoromethanesulfonate,
bis(p-tert-butoxycarbonylmethoxyphenyl)(m-methylphenyl)sulfonium trifluoromethanesulfonate,
bis(p-tert-butoxycarbonylmethoxyphenyl)(o-methylphenyl)sulfonium trifluoromethanesulfonate,
bis(p-tert-butoxycarbonylmethoxyphenyl)(p-methoxyphenyl)sulfonium trifluoromethanesulfonate,
bis(p-tert-butoxycarbonylmethoxyphenyl)(m-methoxyphenyl)sulfonium trifluoromethanesulfonate,
bis(p-tert-butoxycarbonylmethoxyphenyl)(o-methoxyphenyl)sulfonium trifluoromethanesulfonate,
(p-tert-butoxycarbonylmethoxyphenyl)diphenylsulfonium trifluoromethanesulfonate,
(p-tert-butoxycarbonylmethoxyphenyl)bis(p-methylphenyl)sulfonium trifluoromethanesulfonate,
(p-tert-butoxycarbonylmethoxyphenyl)bis(m-methylphenyl)sulfonium trifluoromethanesulfonate,
(p-tert-butoxycarbonylmethoxyphenyl)bis(o-methylphenyl)sulfonium trifluoromethanesulfonate,
(p-tert-butoxycarbonylmethoxyphenyl)bis(p-methoxyphenyl)sulfonium trifluoromethanesulfonate,
(p-tert-butoxycarbonylmethoxyphenyl)bis(m-methoxyphenyl)sulfonium trifluoromethanesulfonate,
(p-tert-butoxycarbonylmethoxyphenyl)bis(o-methoxyphenyl)sulfonium trifluoromethanesulfonate
tris(p-tert-butoxycarbonylmethoxyphenyl)sulfonium p-toluenesulfonate,
bis(p-tert-butoxycarbonylmethoxyphenyl)phenylsulfonium p-toluenesulfonate,
bis(p-tert-butoxycarbonylmethoxyphenyl)(p-methylphenyl)sulfonium p-toluenesulfonate,
bis(p-tert-butoxycarbonylmethoxyphenyl)(m-methylphenyl)sulfonium p-toluenesulfonate,
bis(p-tert-butoxycarbonylmethoxyphenyl)(o-methylphenyl)sulfonium p-toluenesulfonate,
bis(p-tert-butoxycarbonylmethoxyphenyl)(p-methoxyphenyl)sulfonium p-toluenesulfonate,
bis(p-tert-butoxycarbonylmethoxyphenyl)(m-methoxyphenyl)sulfonium p-toluenesulfonate,
bis(p-tert-butoxycarbonylmethoxyphenyl)(o-methoxyphenyl)sulfonium p-toluenesulfonate,
(p-tert-butoxycarbonylmethoxyphenyl)diphenylsulfonium p-toluenesulfonate,
(p-tert-butoxycarbonylmethoxyphenyl)bis(p-methylphenyl)sulfonium p-toluenesulfonate,
(p-tert-butoxycarbonylmethoxyphenyl)bis(m-methylphenyl)sulfonium p-toluenesulfonate,
(p-tert-butoxycarbonylmethoxyphenyl)bis(o-methylphenyl)sulfonium p-toluenesulfonate,
(p-tert-butoxycarbonylmethoxyphenyl)bis(p-methoxyphenyl)sulfonium p-toluenesulfonate,
(p-tert-butoxycarbonylmethoxyphenyl)bis(m-methoxyphenyl)sulfonium p-toluenesulfonate, or
(p-tert-butoxycarbonylmethoxyphenyl)bis(o-methoxyphenyl)sulfonium p-toluenesulfonate.

11. A chemically amplified positive resist composition according to claim 1, comprising an admixture of (A) about 150 to 700 parts of an organic solvent, (B) about 70 to 90 parts of an alkali soluble resin, (C) optionally about 5 to 40 parts of a dissolution inhibitor having an acid labile group, in the case of the three component system, (D) about 1 to 15 parts of a sulfonium salt of formula (1), and optionally, (E) optionally about 0.5 to 15 parts of another photo acid generator.

12. A chemically amplified positive resist composition according to claim 2, wherein the organic solvent is a ketone, an alcohol, an ether, an ester or a mixture thereof.

13. A chemically amplified positive resist composition according to claim 2, wherein the organic solvent is cyclohexanone, methyl-2-n-amylketone, methoxybutanol, 3-methyl-3-methoxybutanol, 1-methoxy-2-propanol, 1-ethoxy-2-propanol, glycol monomethyl ether, ethylene glycol monomethyl ether, propylene glycol monoethyl ether, ethylene glycol monoethyl ether, propylene glycol dimethyl ether, diethylene glycol dimethyl ether, propylene glycol monomethyl ether acetate, propylene glycol monoethyl ether acetate, ethyl lactate, ethyl pyruvate, butyl acetate, methyl 3-methoxypropionate and ethyl 3-ethoxypropionate.

14. A chemically amplified positive resist composition according to claim 2, wherein the alkali soluble resin is a copolymer of hydroxystyrene and styrene, tert-butyl acrylate, tert-butyl methacrylate, maleic anhydride or di-tert-butyl maleate.

15. A chemically amplified positive resist composition according to claim 2, wherein the acid labile group is a tert-butyl, tert-butoxycarbonyl, tetrahydropyranyl, methoxymethyl, trimethylsilyl, or tert-butyldimethylsilyl group.

16. In a method for the production of an image on a substrate, comprising developing a substrate which has been coated with a chemically amplified positive resist composition and exposed to radiation, the improvement wherein the chemically amplified positive resist composition is one of claim 1.

* * * * *